(12) United States Patent
McCormick et al.

(10) Patent No.: US 11,162,844 B2
(45) Date of Patent: Nov. 2, 2021

(54) SNAPSHOT MULTISPECTRAL IMAGER FOR MEDICAL APPLICATIONS

(71) Applicant: Surface Optics Corporation, San Diego, CA (US)

(72) Inventors: Kyle Ryan McCormick, San Diego, CA (US); Jaclyn Nascimento, San Diego, CA (US); Mark Dombrowski, Escondido, CA (US)

(73) Assignee: Surface Optics Corp., San Diego, CA (US)

( * ) Notice: Subject to any disclaimer, the term of this patent is extended or adjusted under 35 U.S.C. 154(b) by 0 days.

(21) Appl. No.: 16/291,255

(22) Filed: Mar. 4, 2019

(65) Prior Publication Data

US 2021/0172797 A1    Jun. 10, 2021

(51) Int. Cl.
| | |
|---|---|
| *G01J 3/26* | (2006.01) |
| *G01J 3/28* | (2006.01) |
| *G01J 3/02* | (2006.01) |
| *G01J 3/447* | (2006.01) |
| *A61B 5/1455* | (2006.01) |
| *A61B 5/00* | (2006.01) |
| *G01J 3/36* | (2006.01) |

(52) U.S. Cl.
CPC ........ *G01J 3/2823* (2013.01); *A61B 5/14551* (2013.01); *G01J 3/0208* (2013.01); *G01J 3/447* (2013.01); *A61B 5/14558* (2013.01); *A61B 5/443* (2013.01); *G01J 3/36* (2013.01); *G01J 2003/2826* (2013.01)

(58) Field of Classification Search
CPC ..... G01J 3/28; G01J 3/02; G01J 3/447; A61B 5/1455; G02B 5/20; G02B 13/00; G06T 7/60; G06K 9/20; H04N 5/33
See application file for complete search history.

(56) References Cited

U.S. PATENT DOCUMENTS

2010/0056928 A1 *  3/2010  Zuzak ................. A61B 5/0071
                                                     600/476
2013/0342680 A1 * 12/2013  Zeng ...................... H04N 5/332
                                                     348/135

* cited by examiner

*Primary Examiner* — Abdullahi Nur
(74) *Attorney, Agent, or Firm* — Insigne PC (57) ABSTRACT

The present invention is a camera with video-rate acquisition and processing for medical imaging applications. In particular, the invention is used to determine the health of a body area by quantitatively measuring blood oxygen levels and melanin content from a real-time video image of a body segment. In certain embodiments, a camera comprises an objective lens; a filter tray located at an aperture stop of the objective lens, wherein the filter tray comprises a plurality of elements, each element passes a spectral band of light; a micro-lens array located at an exit pupil of the objective lens comprising a plurality of micro lenses to form an image plane, wherein the objective lens produces a focused image at the image plane; and a focal plane array comprising a plurality of sensors, wherein each sensor receives light from at least one micro-lens of the micro-lens array.

4 Claims, 11 Drawing Sheets
(4 of 11 Drawing Sheet(s) Filed in Color)

SNAPSHOT MULTISPECTRAL IMAGER FOR MEDICAL APPLICATIONS

CROSS-REFERENCE TO RELATED APPLICATION

The present application claims priority to U.S. patent application Ser. No. 11/774,599 filed on filed on Jul. 7, 2007, entitled "Spatially corrected full-cubed hyperspectral imager," which issued as U.S. Pat. No. 7,433,042, the entire disclosures of which are incorporated by reference herein.

BACKGROUND OF THE INVENTION

1. Field of Invention

This invention relates to spectrometry and, more particularly, to multispectral imaging.

2. Description of Related Art

There are hyperspectral imagers designed to quantitatively measure the health of skin and blood of specific bodily areas. Implementation often requires spatially scanning a specific body area to resolve the spectra of the imaged area. Consequently, scanning approaches require longer integration time on the order of multiple seconds and the absence of movement. Further, processing image data using a filter wheel, scannable filter set, or selective illumination inherently restrict processing frame rate to the acquisition frame rate of the hyperspectral imagers considering how multiple frames are required to generate a full output image.

Prior imaging systems have poor integration times. Specifically, current imagers rotate filters, take multiple images using scanning techniques, and stack the images. Prior art implementations in diagnostics require obtaining an image from a scan to resolve spectra of a scene of interest, e.g., a body area. If a subject moves even slightly, the overall image becomes smeared and the spectral response in turn is falsely modified. Therefore, single frame, real-time measurements at video-rate acquisition and processing area useful in time-sensitive situations, such as surgery, in which detection of a poorly perfused area that is caught quickly can help improve patient outcomes. As a result of using scanning techniques, the output image will have a large spatial resolution, but limited real-time temporal resolution and thus, lose the ability to resolve the images in real time. With increased integration time, the imager is unable to identify objects in a single image, especially if image acquisition is disrupted by object movement. A push-broom scanner obtains images with spectroscopic sensors but require time to scan a scene and produce large data cubes. Both scanning time and large data prohibit applying such in time-sensitive environments such as clinical, agricultural and industrial processing.

Certain hyperspectral imagers and push-broom cameras increase processing and analysis time by reducing the image data by identifying key spectral wavelengths optimal for characterizing objects of interest. These imagers and cameras, however, have limited resilience to imaging jitter and motion to produce a clear spectral profile.

SUMMARY OF THE INVENTION

The present invention overcomes these and other deficiencies of the prior art by providing a snapshot multispectral imager with video-rate acquisition and processing for diagnostic medical imaging. For example, the invention is used to determine the health of skin and blood in a specific body area by quantitatively measuring blood oxygen levels from a real-time video image. The invention provides a real-time, multispectral imaging system that uses the division of wavefront technology to create a multiband image obtained in a single shot or snapshot. The snapshot multispectral imager enables measuring spectra from a single frame rather than measuring spectra averaged over multiple frames. Further, the imager enables the user to image events of shorter time scales while also using data from the same point in time.

In an exemplary embodiment of the invention, an image is divided into spectral bands of wavelengths. Specifically, the aperture stop is divided into a plurality of spectral bands, preferably sixteen (16) spectral bands, before each band is reimaged. The snapshot multispectral imager uses the division of wavefront technology to create a multiband image obtained from a single frame which alleviates the need for time-consuming scanning techniques subject to object movement disruption.

The snapshot multispectral imager is optimized for measuring parameters of blood and skin to determine overall health of a body segment for multiple medical applications. A body segment refers to a bodily area that can be accessed for imaging, for example, a hand, a finger, a foot, or another anatomical section. In an exemplary application, the invention identifies areas within a body segment in which blood oxygen, melanin, skin thickness, or a combination thereof varies. For example, applying a tourniquet to an arm or a finger would show oxygen saturation level decreases as blood is exchanged but not circulated away from a cuffed area. One benefit of the invention is identifying an area of blood flow blockage or decreased oxygenated blood flow. The snapshot multispectral imager system resolves the difference between oxygenated hemoglobin and deoxygenated hemoglobin by calculating the light reflectance of a body segment.

In specific embodiments of the invention, a snapshot multispectral imager system comprises an objective lens; a filter tray placed at an aperture stop of the objective lens, wherein the filter tray has a plurality of elements, each element passes a band of light; a micro-lens array (MLA) placed at an exit pupil of the objective lens comprises a plurality of micro lenses and forms an image plane, wherein the objective lens produces a focused image at the image plane; a focal plane array (FPA) having a plurality of sensors, wherein each micro-lens re-images the filter tray elements onto the sensors; wherein all sensors receive the same image and each sensor receives light from at least one micro-lens of the MLA; a frame grabber receiving the image and sending the image to a computer; a computer having a frame processing unit, a calculation unit, at least one display, and a output parameter.

In an embodiment of the invention, a camera comprises: an objective lens; a filter tray located at an aperture stop of the objective lens, wherein the filter tray comprises a plurality of elements, each element passes a spectral band of light, wherein the filter tray has filter tray elements for spectral bands tailored to a medical indicator of interest; a micro-lens array (MLA) located at an exit pupil of the objective lens comprising a plurality of micro lenses to form an image plane, wherein the objective lens produces a focused image at the image plane; and a focal plane array (FPA) comprising a plurality of sensor arrays, wherein each sensor array receives light from at least one micro-lens of the MLA. The filter tray comprises a bandpass filter with a range of 400 nm to 950 nm. The filter tray comprises a filter covering a non-continuous range of wavelengths between 400 nm and 950 nm. The FPA divides and filters an image into a plurality of spectral bands. The plurality of spectral bands includes at least one spectral band that overlaps with another spectral band. Each of the plurality of spectral bands does not overlap with any other spectral band. The filter tray comprises a polarizer. The filter tray is detachably coupled to the objective lens.

In another embodiment of the invention, a system comprises the camera and a computer comprising software and/or an embedded processor configured to determine a parameter. The parameter is selected from the group consisting of: hemoglobin oxygenation level, melanin content, skin thickness, and a combination thereof. A display indicates oxygenated and/or deoxygenated hemoglobin, preferably as a function of time; unsaturated hemoglobin, semi-saturated hemoglobin, and saturated hemoglobin; melanin content; and/or skin thickness.

In another embodiment of the invention, a method comprises the steps of: passing an image through a first filter tray and an objective lens; focusing, via the objective lens, the image onto a micro-lens array (MLA) comprising a plurality of micro lenses; re-imaging the image, via each one of the plurality of micro lenses, onto each one of a plurality of sensors within a focal plane array (FPA); filtering each re-image associated with each one of the plurality of micro lenses into a number N of spectral bands, where N is equal to or greater than two; generating an image for each spectral band; and processing the generated images for each spectral band to determine a parameter. The parameter is selected from the group consisting of: hemoglobin oxygenation level, melanin content, skin thickness, and a combination thereof. The method may further comprise the step of interchanging the first filter tray with a second filter tray. The method may further comprise the step of displaying oxygenated and/or deoxygenated hemoglobin, melanin content, skin thickness, or a combination thereof.

One advantage is that the invention obtains a snapshot image in real-time and outputs a measurement (e.g., hemoglobin oxygenation response) much quicker than using scanning techniques. Another advantage is that the invention is resilient to jitter and motion during image acquisition. The invention provides higher quality, clearer images even with slight motion during image acquisition. Further, faster video-rate image acquisition and processing of a single frame would make obtaining accurate diagnostic images from an uncooperative patient, such as a child, more feasible. Another advantage of the invention is that it uses interchangeable filters customized to a particular medical diagnostic application.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

The patent or patent application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Preferred embodiments of the present invention and their advantages may be understood by referring to FIGS. 1-11. The described features, structures, or characteristics of the invention may be combined in any suitable manner in one or more embodiments. It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The present multispectral imaging system collects spectral, light field and polarization information to improve classification performance by alleviating the need to separate hundreds of continuous spectral bands to resolve an image. Instead, it selects a handful of feature wavelengths to achieve higher accuracy and faster processing than imagers using the full spectra. In particular, the invention uses filters to collect only established spectral wavelengths relevant to a specific application, e.g., medical application, and further increases classification accuracy by incorporating features extracted from polarization and light-field data. Further, the invention provides video-rate acquisition and processing of up to 30 frames per second (fps), which is the ideal platform for researchers seeking a mature spectral imaging solution for production level application. Accordingly, the term image as used herein includes video images. The multi-dimensional datasets are captured and processed at video rates so the snapshot multispectral imager can be applied to dynamic and online monitoring environments.

The present invention is particularly well-suited for diagnostic medical imaging. In various applications, the invention is used to characterize an area and identify a boundary delineating healthy tissue and unhealthy tissue in a body segment. Specifically, the invention measures parameters such as, but not limited to hemoglobin oxygenation level and melanin content, which are important for mapping the areas influencing wound healing in a body segment affected by burn, an ulcer, or diabetes. As a secondary effect, the measured spectral bands and reflection properties determine other parameters including, but not limited to, skin thickness, oncological markers, and inflammatory markers. Simultaneously measuring variations in blood oxygen level and skin thickness in a body segment helps determine areas with proper oxygenated hemoglobin (healthy tissue) and areas starved of oxygen (unhealthy tissue) that would limit wound healing capacity. The present invention provides a non-invasive device and technique for measuring blood oxygen level, melanin content, and skin thickness permitting, among other things, classification of burn sites according to size, severity, patterns of blood oxygen in affected sites for diagnostic purposes.

Another application includes using the present invention in the field of general wound care, and more specifically, in diagnosis and management of diabetic foot or foot ulcer. Snapshot multispectral imaging system identifies and preventatively identifies an area of concern. The determination of diabetic foot or foot ulcer depends on the ability to identify and measure blood oxygenation. For diabetic foot, there is an initial reduction of blood flow which in turn reduces the oxygenation at the site. By measuring this decreased blood oxygenation level, a medical professional can quickly identify risk regions susceptible to disease. Other applications of the snapshot multispectral imager are not limited to accessing burn sites, diabetic foot, and ulcers.

Figure 1:
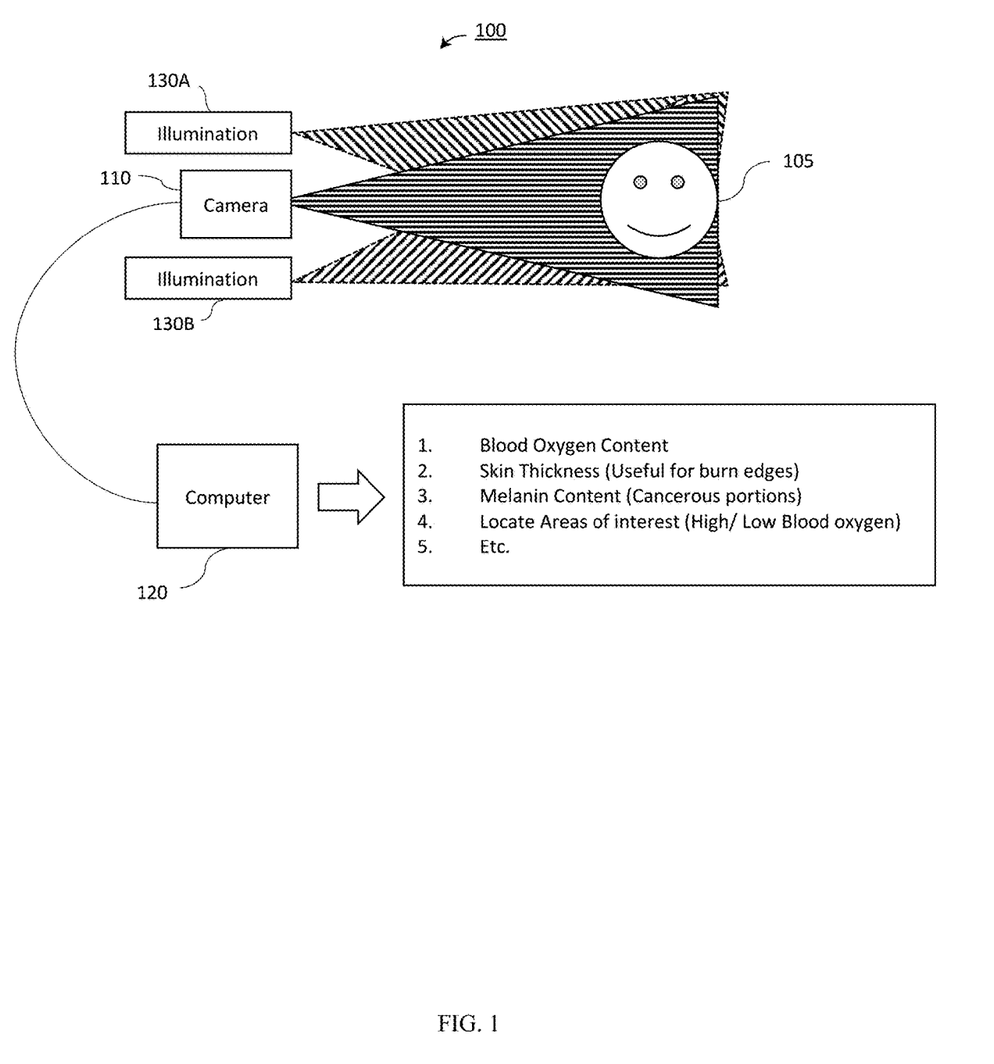
FIG. 1 shows a schematic of a snapshot multispectral imager system.

FIG. 1 depicts a multispectral imaging system 100 according to at least one embodiment of the invention. The multispectral imaging system 100 comprises a camera 110, a computer 120, and one or more optional illumination sources 130A-B (only two are shown). The camera 110 is directed to image a scene of interest 105. In an embodiment of the invention, camera 110, computer 120 and optional illumination sources 130A-B, may be integrated into a single housing. In another embodiment of the invention, the computer 120 is a personal computer, laptop, smartphone, or tablet. The optional illumination sources 130A-B may be optimized according to several spectral bands and bandwidths (e.g., FIGS. 7, 8, and 10). In various examples, an illumination source is any one selected from a group including but not limited to a broadband halogen lamp, LED (white or colored), polarized light, unpolarized light, or any other light source. The computer 120 may communicate with the camera via a wired or wireless communication protocol, the identification and implementation of which are apparent to one of ordinary skill in the art. The computer 120 implements software to, among other things, determine parameters including, but not limited to, blood oxygen content (locate areas of interest with high or low blood oxygen), skin thickness (burn site characterization or diabetic foot diagnosis), melanin content (diagnosis), and other oncological or inflammatory markers. Measuring the skin thickness would be particularly useful in diagnosing a diabetic foot and determining the bounds of a burn site, an ulcer, a tumor, and a metastatic region.

The snapshot multispectral imaging system 100 takes a single frame image, processes and divides the reflectance of an image into more than one spectral band, and preferably at least sixteen (16) spectral bands. The division of measured spectral bands indicate the spectral energy composition of an object in the single frame. The spectral properties of the image are compared to the spectral properties of a reference including, but not limited to, hemoglobin. In addition to measuring blood oxygen content, the snapshot multispectral imager measures other parameters including, but not limited to, skin thickness, and skin absorption, etc. The snapshot multispectral imaging system 100 accounts for its measured parameters and finds the best fit line for the measured spectra. In specific examples, a comparison using two bands show a difference in blood oxygenation. In particular, spectral bands centered on 854 nm and 612 nm have been used to fit a best linear relationship between the reference spectra and the measured spectra (e.g., FIG. 7 and FIG. 8). The rationale for selecting these bands for comparison is because using a 854 nm-centered band results in a relatively flat response for both the oxygenated hemoglobin response and deoxygenated hemoglobin response whereas using a 612 nm-centered band results in a distinct difference between the oxygenated hemoglobin response and the deoxygenated hemoglobin response. In preferred embodiments, the filter trays have elements for spectral bands preselected for a medical application, in which a best fit line resolves peaks in the hemoglobin response.

In a clinical setting, the snapshot multispectral imaging system is used to take a single frame image of a patient's body part at a particular location of interest, to calculate blood oxygenation level, skin thickness, melanin content etc. on a computer.

Figure 2:
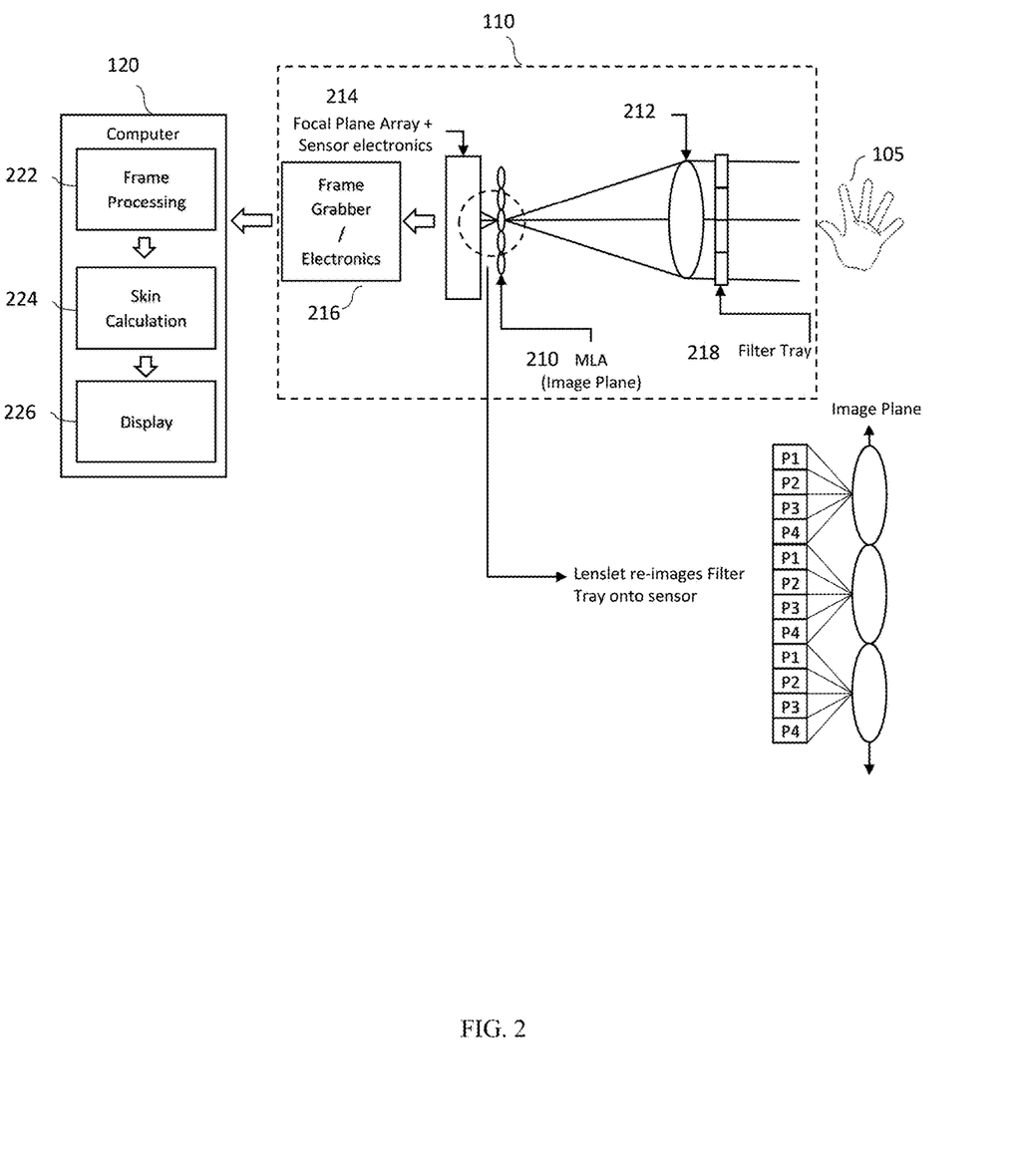
FIG. 2 shows a micro-lens array positioned between an objective lens and a focal plane array and sensor electronics with a representative ray path for image acquisition and processing.

FIG. 2 illustrates the snapshot multispectral imaging system 100 with the camera 110 implementing a micro-lens array (MLA) 210 positioned between an objective lens 212 and a focal plane array (FPA) 214 and sensor electronics 216 with a representative ray path traced for one pixel.

Figure 4:
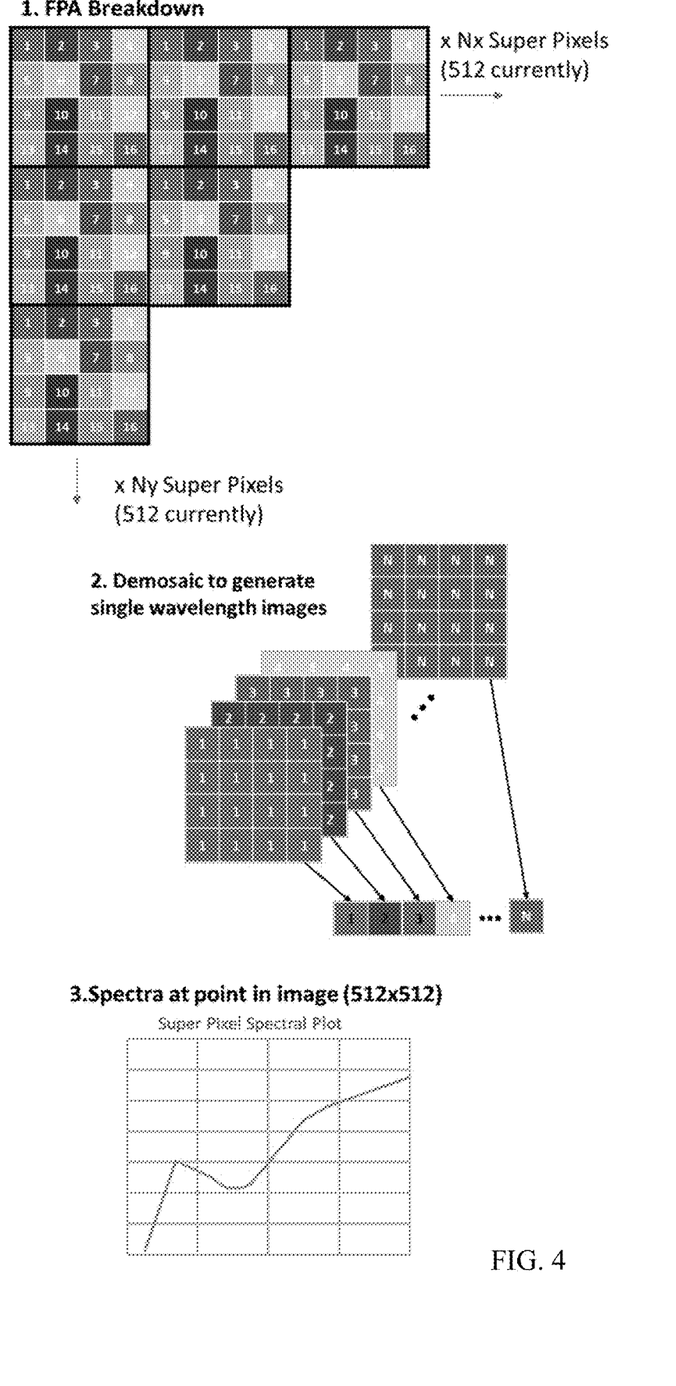
FIG. 4 depicts image acquisition and processing using a snapshot multispectral imager system.

A filter tray 218 is located between the objective lens and the scent of interest 105 and includes spectral filters that divides the acquired image into corresponding spectral bands or wavelengths. This division of wavelengths is shown in FIG. 2 and FIG. 4. The filter tray 218 comprises a bandpass, a narrowband, a broadband, or a custom filter. The custom filter is created by identifying the spectral components of interest and obtaining filters for such spectral bands. Accordingly, the custom filter has various center wavelengths and various filter widths (e.g. compare spectral tables in FIG. 7 and FIG. 10). The custom filter indicated in FIG. 7 has a range between approximately 400 nm to approximately 950 nm, with bands spaced evenly. The custom filter indicated in FIG. 10 have spectral bands that correspond to features of a reflected spectra. Using selected spectral bands that result in expected reference curves are useful in various medical applications. For example, in a surgical application using a dye to image an area of interest in real time, creating a spectral band specific to the dye would enable precise and timely imaging that targets an indicator of interest, e.g. real-time fluorescence image-guided oncologic surgery.

The micro-lens array (MLA) 210 comprises a plurality of micro-lenses, each micro-lens produces a reflectance pattern for one or more sensors; wherein each sensor receives substantially the same image and each sensor of the FPA receives light from one element of the MLA. The MLA further comprises lenslets 210 to re-image the filter tray onto sensors on the FPA 214.

Frame grabber electronics 216 receive the image and send it to the computer 120. More specifically, a method of using a camera 110 includes the step of: a sensor having pixels that collect incident light from a scene; sensor electronics generating an output, wherein the output is a signal from each sensor pixel and a raw signal value corresponding to each sensor pixel; a frame grabber converting the output into a digital signal that the computer can read. In an embodiment of the invention, the computer can read the digital signal via USB/other cable output.

A computer includes a frame processing unit 222, a calculation unit 224, and at least one display 226 to display one or more output parameters. The frame processing unit 222 and/or calculation unit 224 may be implemented in software and/or dedicated hardware via an embedded processor. The calculation unit 224 measures and determines skin-related parameters (e.g., oxygenated hemoglobin level, melanin content, and skin thickness, etc.). Alternatively, the calculation unit 224 measures and determines other parameters including, but not limited to, oncological and inflammatory markers.

Figure 3:
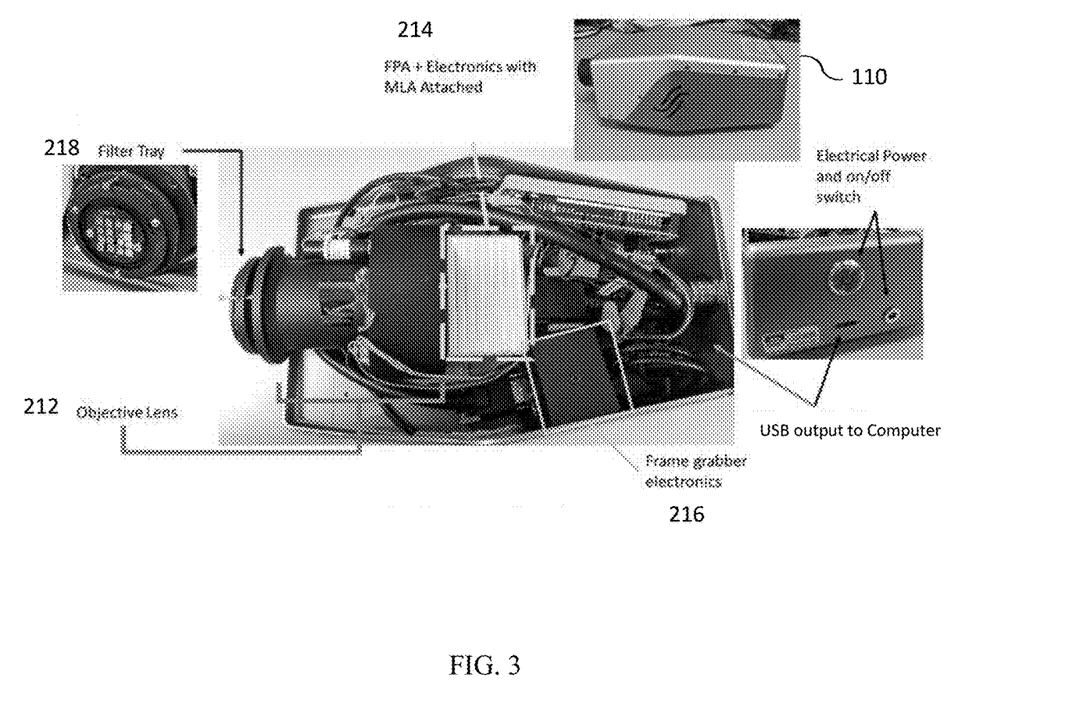
FIG. 3 shows a series of photographs of a snapshot multispectral imager system.

FIG. 3 shows photographs a prototype of the camera 110 according to an embodiment of the invention. The camera 110 includes the objective lens 212 to produce a focused image at an image plane; the filter tray 218 placed at the aperture stop of the objective lens 110, each filter tray element passes a spectral band of light; the MLA 210 comprising a plurality of micro lenses placed at the exit pupil of the objective lens 212, each micro lens passes a spectral band of light; the micro-lenses are attached to the FPA 214 with sensor electronics, each micro-lens re-images the filter tray elements onto sensors on the FPA 214; wherein all sensors receive substantially the same image and each sensor receives light from one element of the MLA. Frame grabber electronics 216 receive the image and sends it to a computer. The camera 110 further comprises a power interface 312 for receiving power from an external source, a power switch 314, and a universal serial bus (USB) interface 316 to communicate with the computer 120. In other embodiments of the invention, the power interface 312 may be replaced with a rechargeable battery for power supply. The USB interface may be replaced with any other type of communications interface, whether currently known or developed later, wired or wireless, permitting communication between the camera 110 and the computer 120. In FIG. 3, the lenslets 210 are not visible because it is mounted to the sensor module of the FPA 214 with the lens attached.

In an embodiment of the invention, the filter tray 218 positioned at the aperture stop of the objective lens 212 is customized for a particular application. For example, a particular filter tray 218 comprises multiple filter tray elements for certain respective spectral bands preselected for a specific application, e.g. medical diagnostic. In other words, the filter tray 218 can be easily interchanged or replaced with another filter tray 218 depending on the specific application. Hence, the snapshot multispectral imaging system 100 can be easily to re-tasked for different applications requiring different wavelengths for analysis. For example, for use in measuring hemoglobin oxygenation level, the filter tray comprises filter tray elements specific to capturing oxygenated and deoxygenated hemoglobin spectra (e.g., FIGS. 7 and 10). In another example, for use in measuring melanin content, the filter tray comprises filter tray elements specific to capturing melanin spectra (e.g., FIGS. 7 and 10). In other non-limiting examples, the filter tray includes other filter tray elements specific to capturing spectra for an indicator of interest.

FIG. 4 depicts image acquisition and processing according to an embodiment of the invention. The FPA 214 include sensors for various discreet bandpass filters that form a filter matrix. In this example, the 4×4 array forms one super-pixel. In other examples, an N×N array forms one super-pixel, where N is equal to or greater than two. The upper and lower limits of N depend on the overall sensor size and the required resolution. In this example, the N×N array equals a 4×4 super-pixel whereby a 2048×2048 sensor array is divided into a plurality of spectral bands to form 512×512 spectral images.

In one embodiment, the FPA forms at least 32 super pixels and 512 elements. A 4×4 array is shown to simply the illustration. In the 4×4 array, sub-pixels correspond to filter matrix elements number 1 through 16. The 16-element filter matrix pattern is repeated across the entire image array. A regular packed pattern of super-pixels fills the image array area. Light passing through one micro lens fills one super-pixel area. The camera 110 enables each filter in the MLA 210 to be imaged to the same point in the scene for each pixel, producing more than one co-registered spectral images, preferably sixteen (16) spectral images. The frame processing unit 222 uses image demosaicing to generate spectral images, wherein each spectral image is formed from the sum of unique wavelengths that have been grouped. The spectral signature at individual points in the spectral image is plotted as a super pixel scatter plot.

Figure 5:
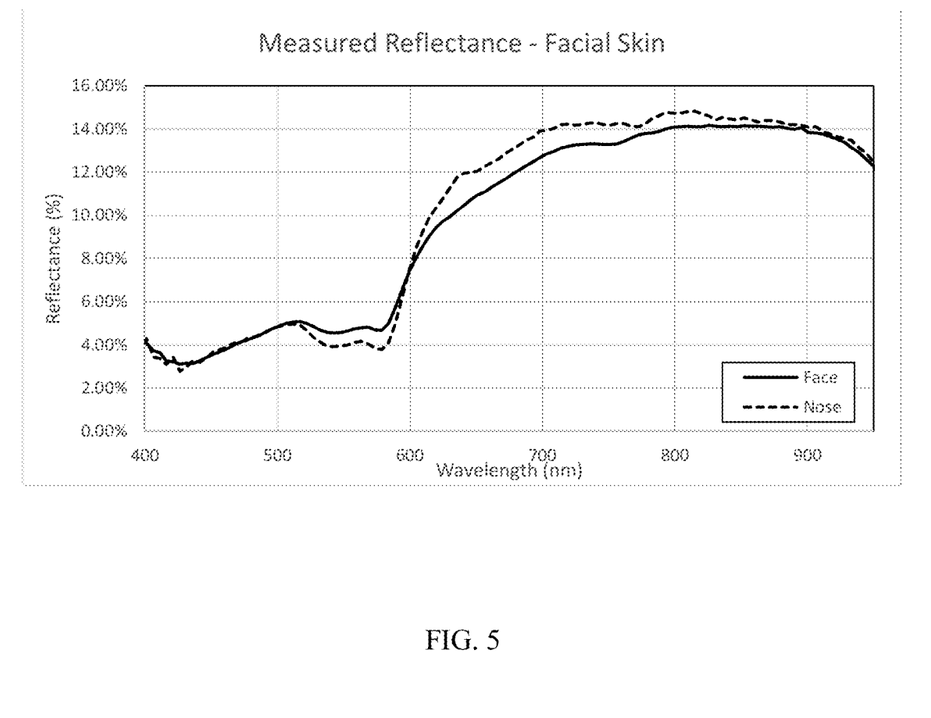
FIG. 5 shows measured reflectance of facial skin using a snapshot multispectral imager system.

FIG. 5 shows measured reflectance of facial skin using a snapshot multispectral imaging system. The example shows reflectance (percentage) as a function of wavelength (nm). The results validate that measured reflectance of facial skin is consistent with expected reflectance of reference nose skin as cited in the literature. Elli Angelopoulou, "The Reflectance Spectrum of Human Skin," December 1999.

Figure 6:
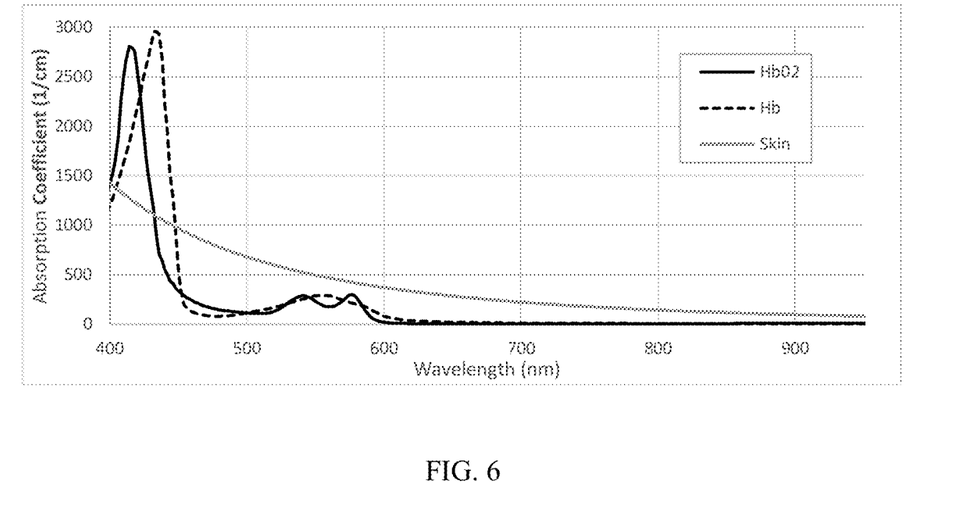
FIG. 6 shows measured hemoglobin oxygenation levels and skin absorption profiles using a snapshot multispectral imager system.

FIG. 6 depicts measured hemoglobin and skin absorption profiles using the snapshot multispectral imaging system. The results show the absorption profiles for oxygenated and deoxygenated hemoglobin and skin melanin. Notably, the snapshot multispectral imager measures detectable oxygen content of blood as indicated by the "W" shaped-signature in the oxygenated hemoglobin curve between approximately 500 nm and approximately 600 nm and the lack of a signature in the deoxygenated hemoglobin curve.

Figure 7:
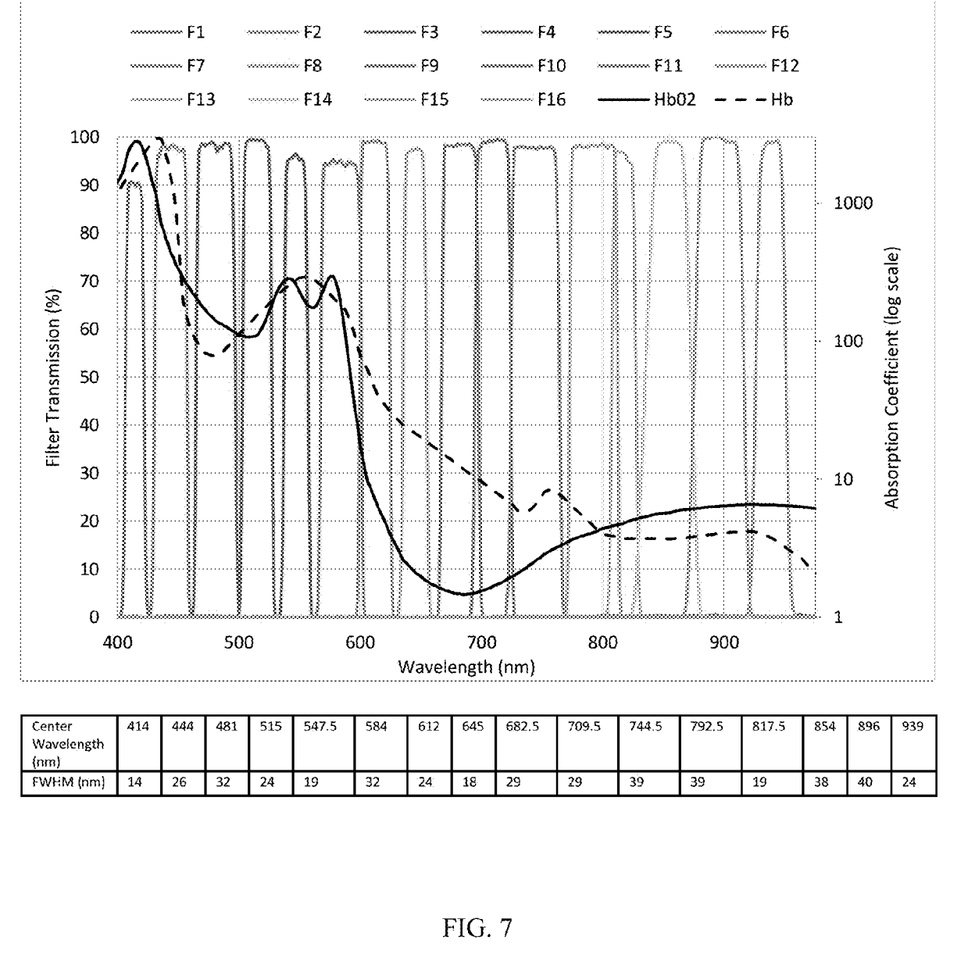
FIG. 7 shows oxygenated and deoxygenated hemoglobin absorption profiles superimposed on a general filter transmission.

FIG. 7 shows oxygenated and deoxygenated hemoglobin absorption profiles superimposed on a general filter tray transmission. In certain examples, the snapshot multispectral imager is a light field visible infrared apparatus (LVIRA). The graph shows filter transmission (left y-axis) as a function of wavelength and absorption coefficient (right y-axis) as a function of wavelength. In certain application examples, a snapshot multispectral imager compares hyperspectral data showing a target spectra against a reference spectra or absorption curve. For general applications including, but not limited to, spectral tracking and spectral identification, the multispectral imager system functions with a general filter tray having a range of approximately 400 nm and approximately 950 nm. FIG. 7 also shows a table of exemplary spectral bands expressed as center wavelength and full-width at half maximum (FWHM). In various examples, the filter tray includes alternative center wavelengths and alternative full-width at half maximum values.

Figure 8:
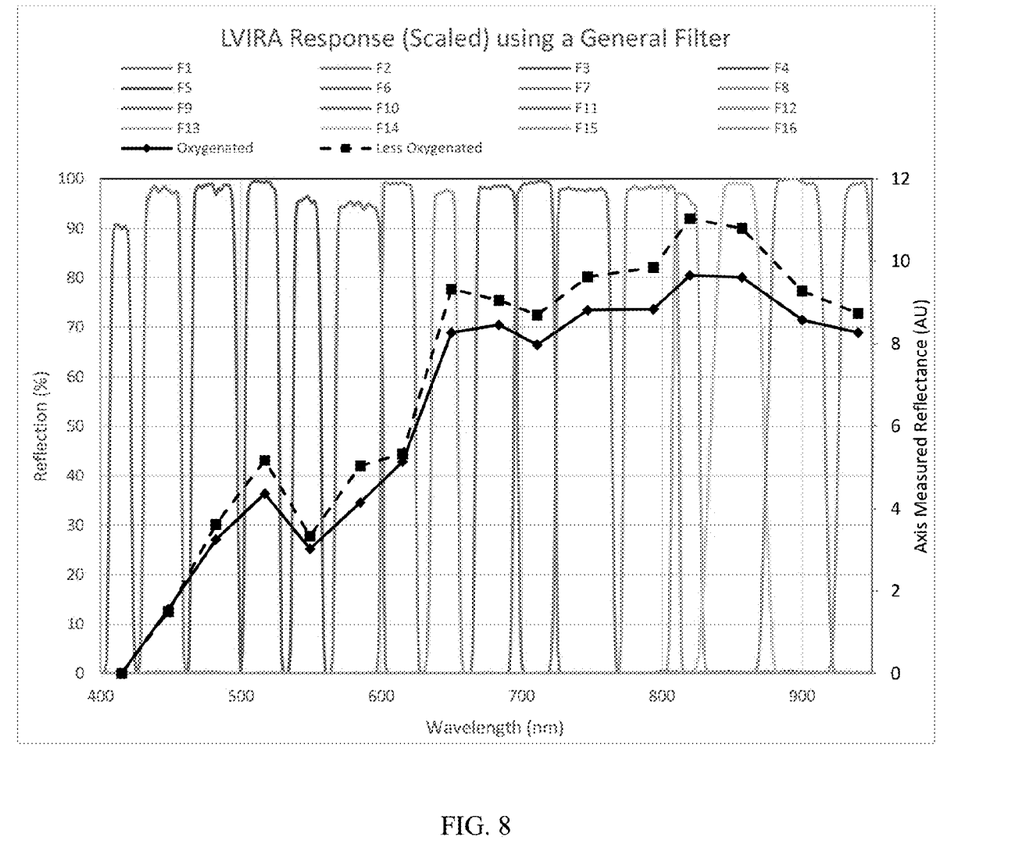
FIG. 8 shows scaled oxygenated and deoxygenated hemoglobin responses superimposed on a general filter transmission.

FIG. 8 shows scaled responses from oxygenated and deoxygenated hemoglobin using a general filter. The graph shows filter transmission (left y-axis) as a function of wavelength and measured reflectance (right y-axis) as a function of wavelength. In particular, FIG. 8 shows the measured response using a general filter tray. Within the spectral range of approximately 500 nm and approximately 600 nm, closer to the 550±25 nm window a double peak in the oxygenated hemoglobin appears to be less clear and in lower resolution.

In alternative instances, a response associated with oxygenated hemoglobin comprises at least one peak between approximately 500 nm and approximately 650 nm. In certain examples, a response comprising at least one peak between approximately 500 run and approximately 650 nm indicates oxygenated hemoglobin. In other examples, a response lacking at least one peak between approximately 500 nm and approximately 650 nm indicates deoxygenated hemoglobin.

Figure 9:
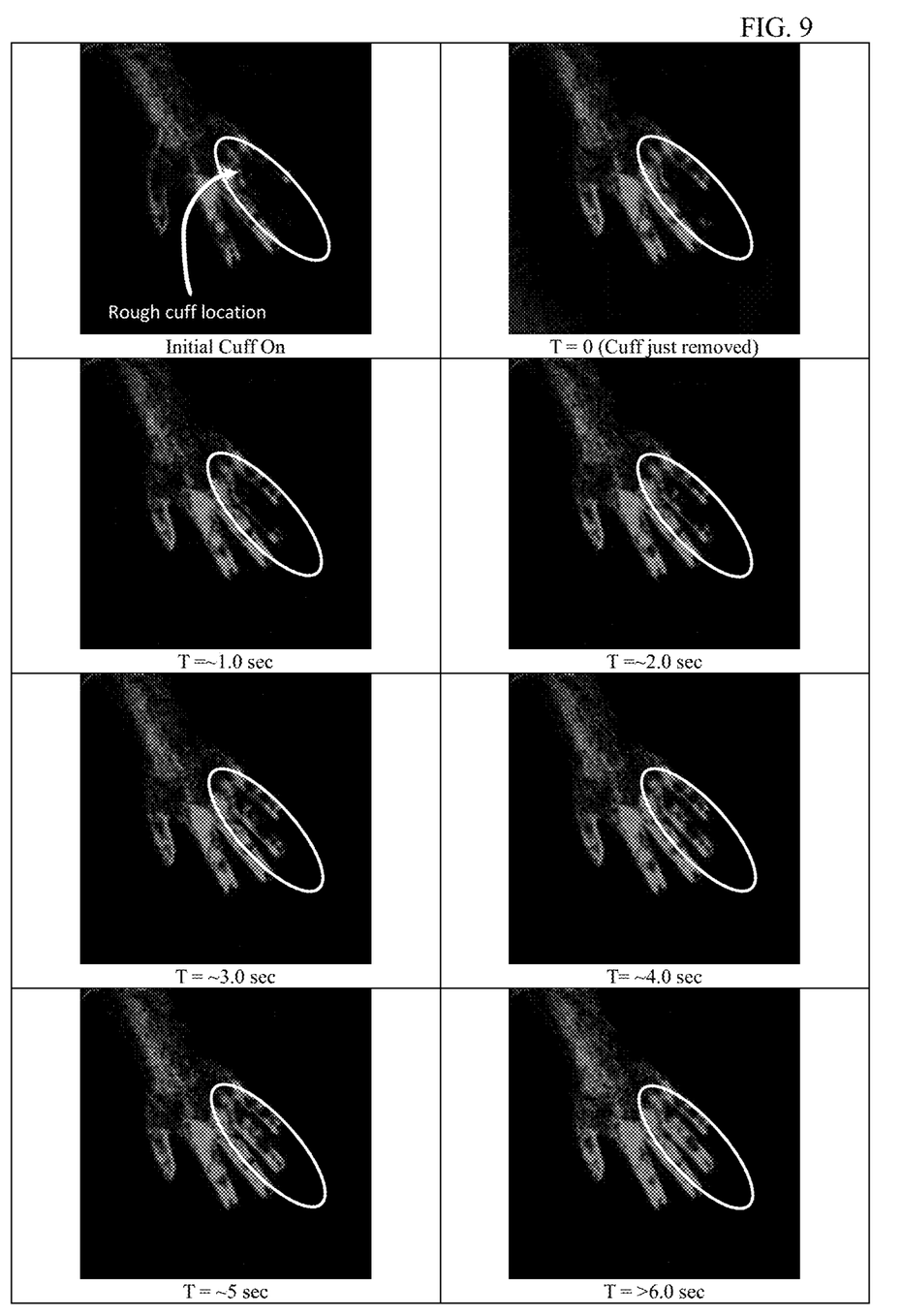
FIG. 9 shows exemplary video frames of finger cuff removal output.

FIG. 9 shows exemplary video frames of finger cuff removal taken by a snapshot multispectral imager system. In these examples, the area of interest is circled. FIG. 9 shows the latest video frames in which blood flow was cut off to a finger using a cuff and the snapshot multispectral imager images part of the oxygenated and deoxygenated hemoglobin. For instance, the frames show various timestamps at 1 second intervals from initial cuff on to post-6 seconds following cuff removal. In other instances, the frames show timestamps at other time points and other inter-frame intervals designated by the user. The snapshot multispectral imaging system functions with a general filter tray.

The snapshot multispectral imager includes a computer having a frame processing unit wherein analysis software processes a difference in oxygenated hemoglobin level in a finger with and without a cuff, and oxygenated hemoglobin level re-entering the finger upon cuff removal and post cuff removal.

Figure 10:
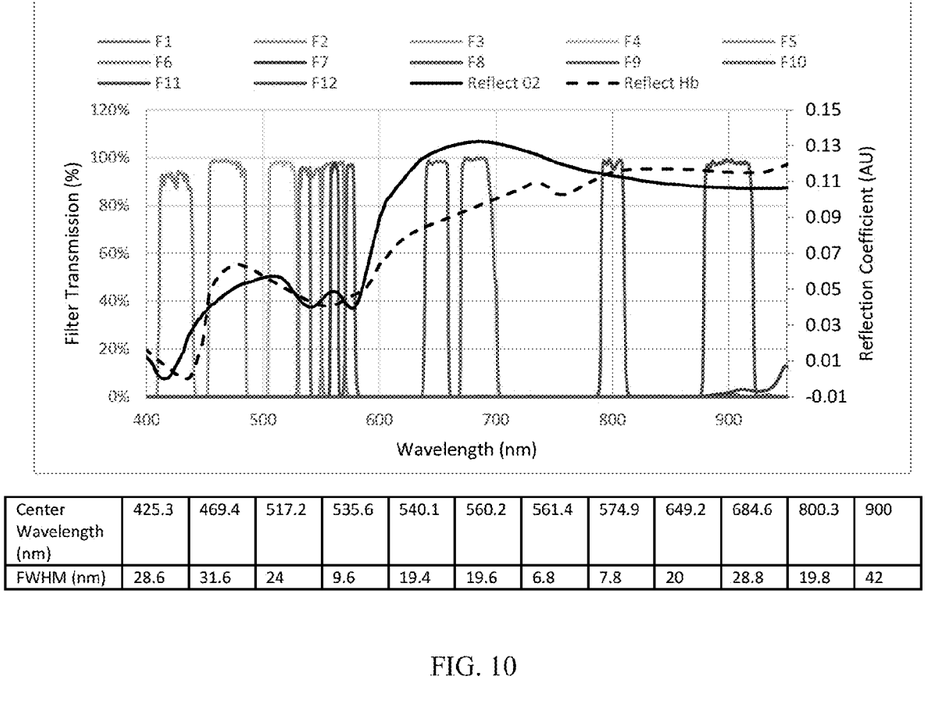
FIG. 10 shows oxygenated and deoxygenated hemoglobin curves superimposed on a custom filter transmission.

FIG. 10 depicts oxygenated and deoxygenated hemoglobin curves superimposed on a custom filter transmission. The graph shows filter transmission (left y-axis) as a function of wavelength and reflection coefficient (right y-axis) as a function of wavelength. The snapshot multispectral imaging system functions with a custom filter tray having a spectral range for reflecting responses corresponding to hemoglobin oxygenation level, melanin content, variation in skin thickness (e.g., burns and diabetic foot). In certain examples, a response is extracted from a multi-variable solution corresponding to a hemoglobin oxygenation level, a melanin content, a skin thickness, or a combination thereof. FIG. 10 also shows a table of exemplary spectral bands expressed as center wavelength and full-width at half maximum (FWHM). In various examples, the filter tray includes alternative center wavelengths and alternative full-width at half maximum values for certain medical and non-medical applications.

More specifically, the custom filter has a spectral range between approximately 750 nm and approximately 850 nm, wherein an oxygenated hemoglobin response appears. Alternatively, the custom filter includes a spectral range of between approximately 400 nm and approximately 950 nm, wherein a hemoglobin-related peak appears at approximately 500 nm and at approximately 650 nm within ±25 nm. In other instances, at least one hemoglobin-related response peak appears between approximately 500 nm and approximately 650 nm.

In another example, the custom filter includes a spectral range of between approximately 400 nm and approximately 950 nm, wherein a response corresponding to melanin content appears between approximately 700 nm and approximately 900 nm. In specific examples, the melanin response appears uniform. In various examples, a hemoglobin oxygenation level response appears within a spectral range outside of a spectral range associated with a melanin content response. In certain instances, the spectral range associated with a melanin content response is between approximately 700 nm and approximately 900 nm.

In yet another embodiment, the custom filter comprises a spectral range of between approximately 400 nm and approximately 950 nm, wherein a response associated with tissue affected by a burn appears. In another embodiment, the custom filter comprises a spectral range between approximately 400 nm and approximately 950 nm, wherein a response associated with inflammation in diabetic foot appears.

In certain embodiments, the custom filter comprises a plurality of bands divided evenly or unevenly within a spectral range of approximately 400 and approximately 950 nm. In various embodiments, the snapshot multispectral imaging system comprises a spectral identity for a given object in an image, wherein the object is trackable by its spectral identity. Furthermore, a target spectra that is measured is compared to a reference spectra to provide information about an anomaly if a discrepancy exists between the target spectra and the reference spectra. In particular for determining skin thickness discrepancies, a multi-layer skin model is used as the theoretical output curve. This theoretical model contains the medical parameters and solves for them by creating a best fit of the model and measured. With a solution to the theoretical model, the medical parameters can be extracted.

In certain embodiments, the custom filter tray includes at least one overlapping spectral band within a range of approximately 400 nm and approximately 950 nm. Specifically, in FIG. 10, the custom filter tray includes a pair of overlapping spectral bands for the purpose of improving resolution of a response signature, for example, at least one peak present at approximately 500 nm and at approximately 650 nm within ±25 nm in the oxygenated hemoglobin absorption curve. In one example, the overlapping bands have center wavelengths of 535 nm and 540 nm and 560 nm and 561 nm. In other examples, the custom filter tray includes a plurality of slots for inserting a polarizer. In certain examples, there are four (4) slots for accommodating four (4) polarizers. The present invention functions without polarizers for measuring blood oxygen level, melanin content, and skin thickness. Alternatively, the invention including a polarizer would be useful in other medical applications. In various examples, the custom filter tray includes a plurality of spectral bands, each spectral band having a center wavelength and a full-width at half maximum (FWHM). In certain instances, the spectral band overlaps with another spectral band. In other instances, the spectral band does not overlap with another spectral band. The differences in response resolution can be seen when comparing FIG. 8 to FIG. 10.

Figure 11:
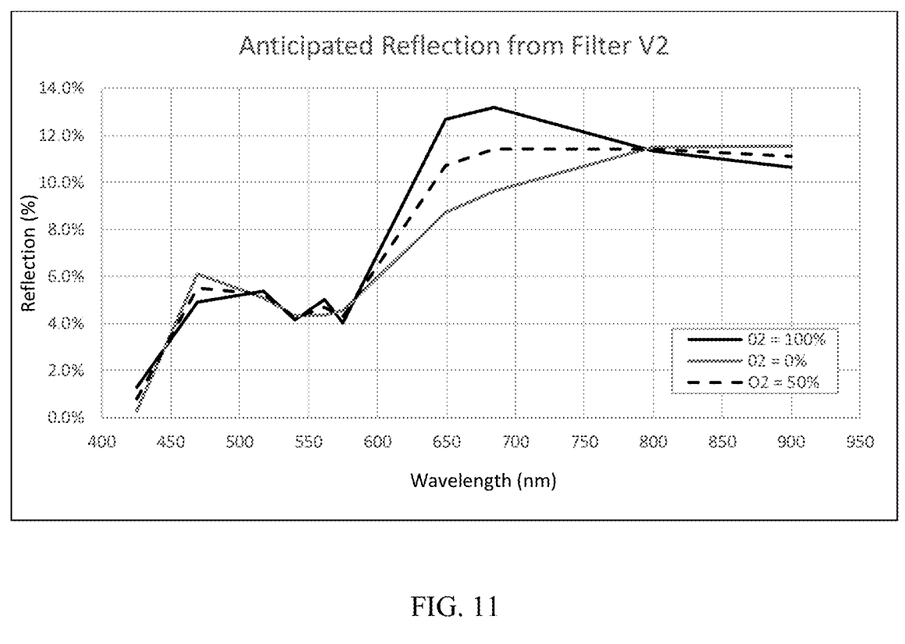
FIG. 11 shows anticipated oxygenated and deoxygenated hemoglobin responses using a custom filter in the snapshot multispectral imager system.

FIG. 11 depicts anticipated responses from unsaturated (0%), semi-saturated (50%), and saturated (100%) oxygenated hemoglobin using a custom filter as shown in FIG. 10. Specifically, the graph shows the reflectance of hemoglobin as a function of wavelength. In particular, the saturated hemoglobin signature comprises at least a peak within the approximately 500-600 nm range, the approximately 650-900 nm range, or both. In particular, the custom filter provides clearer responses (FIG. 10 and FIG. 11) compared to responses provided by the general filter (FIG. 7 and FIG. 8) in terms of a higher resolution of the double peak signature typically associated with oxygenated hemoglobin which would make differentiating oxygenated hemoglobin from deoxygenated hemoglobin easier.

In other examples, it is theoretically possible to filter the FPA to obtain different spectral bands instead of breaking the aperture stop into separate bands and imaging the system. Another method of using a snapshot multispectral imager system comprises the step of: obtaining more than one snapshot multispectral imager; synchronizing the more than one snapshot multispectral imager to capture an image simultaneously. In alternative embodiments, the MLA is positioned on a single sensor.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

The invention claimed is:

1. A method of using a camera comprising the steps of:
    passing an image through a first filter tray and an objective lens, wherein the first filter tray comprises a plurality of first elements, each first element passes a unique spectral frequency band of light preselected for a first diagnostic medical imaging application;
    selecting the unique spectral frequency band that each first element passes based on the following center wavelength values in nanometers (nm), plus or minus 1 percent: 425.3, 469.4, 517.2, 535.6, 540.1, 560.2, 561.4, 574.9, 612.0, 649.2, 684.6, 800.3, 852.0 and 900.0;
    focusing, via the objective lens, the image onto a micro-lens array (MLA) comprising a plurality of micro lenses;
    re-imaging the image, via each one of the plurality of micro lenses, onto each one of a plurality of sensors within a focal plane array (FPA);
    filtering each re-image associated with each one of the plurality of micro lenses into a number N of spectral bands, where N is equal to or greater than two;
    generating an image for each spectral band; and
    processing the generated images for each spectral band to determine a parameter.

2. The method of claim 1, wherein the parameter is selected from the group consisting of: hemoglobin oxygenation level melanin content, skin thickness, and a combination thereof.

3. The method of claim 2, further comprising the step of displaying oxygenated and/or deoxygenated hemoglobin, melanin content, skin thickness, or a combination thereof.

4. The method of claim 1, further comprising the step of interchanging the first filter tray with a second filter tray.

* * * * *